United States Patent
Xiao et al.

(10) Patent No.: US 10,369,108 B2
(45) Date of Patent: Aug. 6, 2019

(54) HOT MELT GRANULATION FORMULATIONS OF POORLY WATER-SOLUBLE ACTIVE AGENTS

(71) Applicant: Mylan Laboratories, Inc., Cannonsburg, PA (US)

(72) Inventors: Chaoju Xiao, Morgantown, WV (US); Boyong Li, Morgantown, WV (US)

(73) Assignee: Mylan Laboratories, Inc., Canonsburg, PA (US)

( * ) Notice: Subject to any disclaimer, the term of this patent is extended or adjusted under 35 U.S.C. 154(b) by 0 days.

(21) Appl. No.: 14/211,144

(22) Filed: Mar. 14, 2014

(65) Prior Publication Data
US 2014/0275242 A1 Sep. 18, 2014

Related U.S. Application Data

(60) Provisional application No. 61/788,142, filed on Mar. 15, 2013.

(51) Int. Cl.
*A61K 9/20* (2006.01)
*A61K 9/16* (2006.01)
*A61K 31/145* (2006.01)

(52) U.S. Cl.
CPC .......... *A61K 9/2013* (2013.01); *A61K 9/1617* (2013.01); *A61K 9/1652* (2013.01); *A61K 9/2018* (2013.01); *A61K 9/2054* (2013.01); *A61K 31/145* (2013.01)

(58) Field of Classification Search
None
See application file for complete search history.

(56) References Cited

U.S. PATENT DOCUMENTS

| | | | |
|---|---|---|---|
| 4,678,809 A | 7/1987 | Phillips |
| 4,681,765 A | 7/1987 | Guley |
| 5,206,264 A | 4/1993 | Marangos |
| 5,665,770 A | 9/1997 | Terao et al. |
| 6,149,941 A | 11/2000 | Schwarz et al. |
| 7,816,403 B2 | 10/2010 | Kennedy |

(Continued)

FOREIGN PATENT DOCUMENTS

| | | |
|---|---|---|
| EP | 0 284 879 A2 | 10/1988 |
| EP | 1 002 535 A1 | 5/2000 |

(Continued)

OTHER PUBLICATIONS

DrugBank Database Disulfiram (DB00822), 2003.*

(Continued)

*Primary Examiner* — Bethany P Barham
*Assistant Examiner* — Barbara S Frazier

(57) ABSTRACT

The presently disclosed subject matter is directed to a granule, wherein the granule has an active agent and a wax dispersed therein, and the granule exhibits excellent friability when compressed to form a pharmaceutical composition. The subject matter disclosed herein is also directed to methods of preparing the granules and the pharmaceutical compositions comprising the granules. The compositions and methods disclosed provide granules and pharmaceutical compositions for immediate release of the active agent and do not substantially prolong the release of the active agent from the granule.

7 Claims, 2 Drawing Sheets

(56) References Cited

U.S. PATENT DOCUMENTS

| | | |
|---|---|---|
| 8,022,095 B2 | 9/2011 | Plachetka |
| 2003/0170312 A1 | 9/2003 | Benameur et al. |
| 2004/0062778 A1 | 4/2004 | Shefer et al. |
| 2004/0115258 A1* | 6/2004 | Stroppolo ............ A61K 9/0056 424/465 |
| 2006/0110444 A1* | 5/2006 | Holm et al. .................. 424/464 |
| 2006/0246080 A1 | 11/2006 | Alibek et al. |
| 2006/0275367 A1* | 12/2006 | Chungi ......................... 424/469 |
| 2008/0050443 A1* | 2/2008 | Kowalski ............ A61K 9/2095 424/490 |
| 2008/0319092 A1 | 12/2008 | Singh |
| 2009/0105125 A1 | 4/2009 | Zhao et al. |
| 2009/0258869 A1 | 10/2009 | Ron et al. |
| 2010/0041689 A1 | 2/2010 | Johnson et al. |
| 2010/0137247 A1 | 6/2010 | Hyde et al. |
| 2010/0227920 A1 | 9/2010 | Ganesan et al. |
| 2011/0003890 A1 | 1/2011 | Schwartz et al. |
| 2011/0111024 A1 | 5/2011 | Mao et al. |
| 2011/0256150 A1 | 10/2011 | Watts et al. |
| 2011/0286927 A1 | 11/2011 | Ratan |
| 2012/0030779 A1 | 2/2012 | Benjamin et al. |
| 2012/0040006 A1 | 2/2012 | Eeckman et al. |
| 2012/0071468 A1 | 3/2012 | John et al. |
| 2013/0034603 A1 | 2/2013 | Hrakovsky |

FOREIGN PATENT DOCUMENTS

| | | | |
|---|---|---|---|
| EP | 2101567 A2 | 9/2009 | |
| EP | 2164518 A1 | 3/2010 | |
| NZ | 545724 A | 11/2007 | |
| RU | 2 068 692 C1 | 11/1996 | |
| WO | WO 84/00887 A1 | 3/1984 | |
| WO | WO 92/19226 A1 | 11/1992 | |
| WO | WO 93/00933 A1 | 1/1993 | |
| WO | WO 96/01127 A1 | 1/1996 | |
| WO | WO 96/39996 A1 | 12/1996 | |
| WO | WO 97/05867 A1 | 2/1997 | |
| WO | WO 97/09976 A2 | 3/1997 | |
| WO | WO9718798 * | 5/1997 | ............ A61K 9/16 |
| WO | WO 99/34784 A2 | 7/1999 | |
| WO | WO 00/78342 A1 | 12/2000 | |
| WO | WO 01/00193 A2 | 1/2001 | |
| WO | WO 01/17522 A1 | 3/2001 | |
| WO | WO 01/51046 A1 | 7/2001 | |
| WO | WO 02/15920 A2 | 2/2002 | |
| WO | WO 02/28349 A2 | 4/2002 | |
| WO | WO 02/056823 A2 | 7/2002 | |
| WO | WO 02/074246 A2 | 9/2002 | |
| WO | WO 03/037313 A2 | 5/2003 | |
| WO | WO 03/075910 A1 | 9/2003 | |
| WO | WO 03/077901 A1 | 9/2003 | |
| WO | WO 03/088965 A1 | 10/2003 | |
| WO | WO 2004/017957 A1 | 3/2004 | |
| WO | WO 2004/022066 A2 | 3/2004 | |
| WO | WO 2005/009338 A2 | 2/2005 | |
| WO | WO 2005/049026 A1 | 6/2005 | |
| WO | WO 2006/021008 A2 | 2/2006 | |
| WO | WO 2006021455 * | 3/2006 | ............ A61K 9/16 |
| WO | WO 2006/044771 A2 | 4/2006 | |
| WO | WO 2007/065016 A3 | 6/2007 | |
| WO | WO 2008/045017 A3 | 4/2008 | |
| WO | WO 2008/089440 A2 | 7/2008 | |
| WO | WO 2008/144888 A1 | 12/2008 | |
| WO | WO 2008/153511 A1 | 12/2008 | |
| WO | WO 2009/020601 A2 | 2/2009 | |
| WO | WO 2009/044294 A3 | 4/2009 | |
| WO | WO 2009/056849 A1 | 5/2009 | |
| WO | WO 2009/109952 A2 | 9/2009 | |
| WO | WO 2010/048446 A2 | 4/2010 | |
| WO | WO2010121321 * | 10/2010 | ............ A61K 9/51 |
| WO | WO 2012/012498 A2 | 1/2012 | |
| WO | WO 2012/012498 A9 | 1/2012 | |
| WO | WO 2012/024616 A1 | 2/2012 | |

OTHER PUBLICATIONS

DrugBank Database (Fenofibrate (DB01039)).*

Pathak et al. (Formulation and optimization of immediate release tablet of an antialcoholic drug by dry granulation method, Int. J. of Comprehensive Pharmacy, 2011, vol. 8, pp. 1-4).*

Kowalski et al. (Application of melt granulation technology to enhance stability of moisture sensitive immediate-release drug product , Int. J. Pharm., 2009, vol. 38, pp. 56-61) (Year: 2009).*

Gohel et al. (Exploration of melt granulation technique for the development of compressed directly compressible adjuvant containing lactose and microcrystalline cellulose, Pharm. Develp. and Tech., 2003, vol. 8, pp. 175-185) (Year: 2003).*

Chowhan et al. in Punch geometry and formulation considerations in reducing tablet friability and their effect on the in vitro dissolution, J. Pharma. Sci., 1992, pp. 290-294 (Year: 1992).*

Ochoa, L., et al., "Preparation of sustained release hydrophilic matrices by melt granulation in a high-shear mixer," *J Pharm Pharmaceut Sci*, 2005, vol. 8(2), pp. 132-140.

* cited by examiner

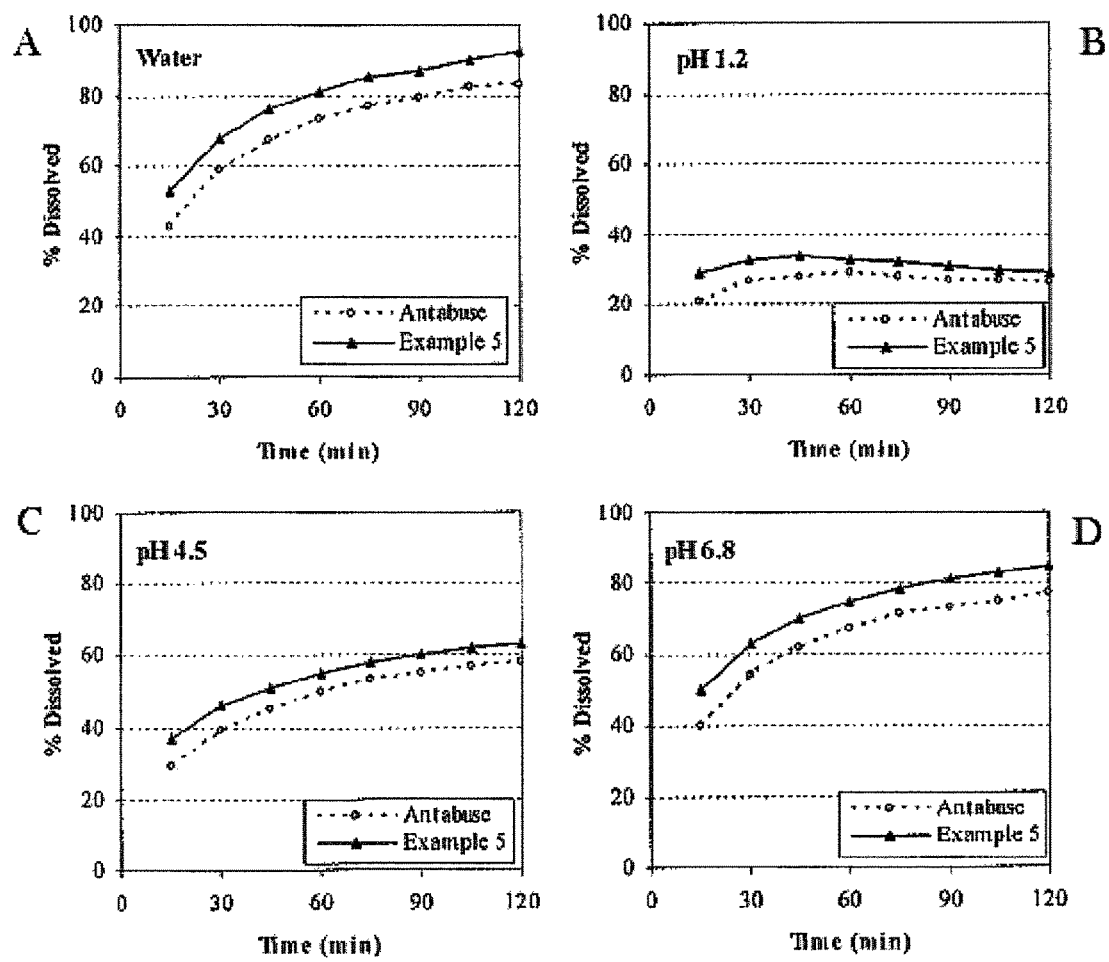
Figure 2 A-D

HOT MELT GRANULATION FORMULATIONS OF POORLY WATER-SOLUBLE ACTIVE AGENTS

CROSS-REFERENCE TO RELATED APPLICATIONS

This application claims the benefit of U.S. Provisional Application No. 61/788,142, filed Mar. 15, 2013, which is hereby incorporated herein in its entirety by reference.

FIELD OF THE INVENTION

The subject matter herein is directed to pharmaceutical hot melt granulation compositions comprising a poorly water-soluble active agent, to the preparation of the compositions and to their uses in therapeutic methods.

BACKGROUND

Granulation is a process for preparing agglomerates from powders such that the agglomerates can be further processed by compressing to form pharmaceutical dosage forms such as tablets. In the absence of granulation, many active ingredient containing powders would not be able to be compressed into tablets having acceptable friability.

Wet granulation is a widely used method of granulation used in tablet and capsule manufacture. Hot melt granulation employs a molten binder to form agglomerates. However, when tablet or capsule ingredients are sensitive to moisture or are unable to withstand elevated temperatures, dry granulation may be employed. In any case, the granules once formed must possess physical characteristics required for the formulation to be compressed into a tablet.

However, it is difficult to combine certain active ingredients with the excipients needed to form granules without also affecting the release profile of the active ingredient from the final formulation containing the granules. The following disclosure addresses this shortcoming of the art.

SUMMARY OF THE INVENTION

The presently disclosed subject matter is directed to a granule, wherein the granule has an active agent and a wax dispersed therein, and the granule exhibits excellent friability when compressed to form a pharmaceutical composition. The subject matter disclosed herein is also directed to methods of preparing the granules and the pharmaceutical compositions comprising the granules. The compositions and methods disclosed provide granules and pharmaceutical compositions for immediate release of the active agent and do not substantially prolong the release of the active agent from the granule.

In an embodiment, the subject matter disclosed herein is directed to a pharmaceutical composition, comprising: a granule, the granule comprising an active agent and a wax material, wherein the active agent has a water solubility of less than 1 mg/ml and the wax material is present in an amount below about 8% (w/w) of the granule.

In an embodiment, the subject matter disclosed herein is directed to a granule comprising a poorly water-soluble active agent and a wax material, wherein the active agent and the wax material are dispersed throughout the granule, wherein the active agent has a water solubility of less than 1 mg/ml and the wax material is present in an amount below about 8% (w/w).

In an embodiment, the subject matter disclosed herein is directed to a tablet comprising compressed granules, wherein the granules comprise from about 2% to below about 8% (w/w) wax material and an active agent having water solubility of less than 1 mg/ml, wherein the tablet has a friability of less than about 1%.

In an embodiment, the subject matter disclosed herein is directed to a method of preparing a granule comprising an active agent having a water solubility less than 1 mg/mL, the method comprising: a) contacting the active agent with a liquid wax material; b) forming a granulation mix comprising the active agent and the wax material; and c) allowing the mixture to cool to prepare the granules or the pharmaceutical compositions comprising the granules.

DESCRIPTION OF THE DRAWINGS

FIGS. 2A-D show dissolution of disulfiram tablets, 500 mg, Example 5 formulation (wet granulation) in comparison with Antabuse® 500 mg in media of various pH values and in water, all with 2% sodium lauryl sulfate, using USP Apparatus II at 100 rpm.

DETAILED DESCRIPTION

Figure 1:
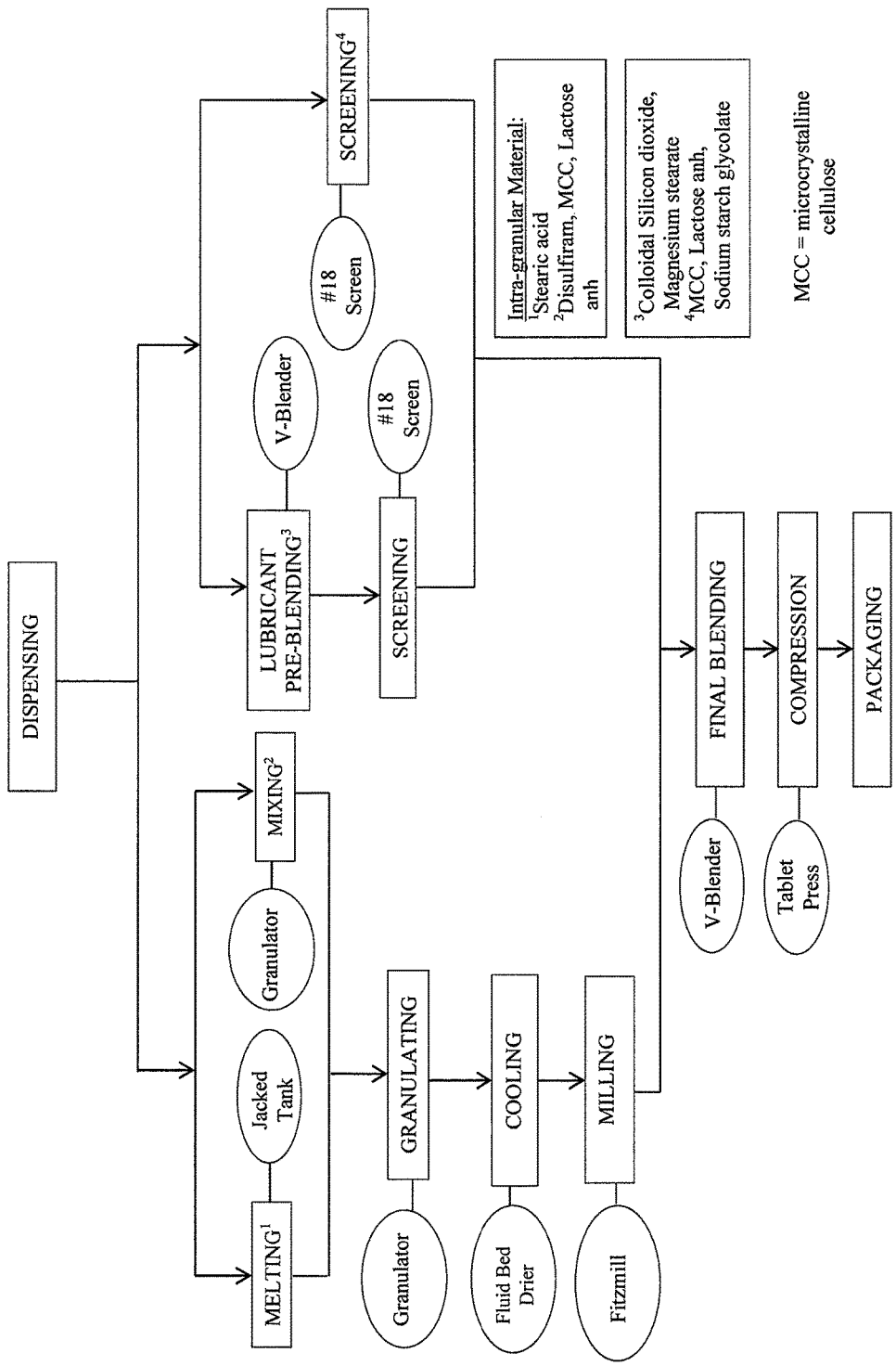
FIG. 1 depicts a flow diagram for preparing a tablet according to one of the methods disclosed herein. The tablet formed by the diagrammed process contains disulfiram, stearic acid, microcrystalline cellulose ("MCC"), lactose anhydrous, sodium starch glycolate, magnesium stearate, and colloidal silicon dioxide.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims.

In the pharmaceutical arts, hot melt granulation is a process generally used for preparing extended release pharmaceutical preparations. The process employs high levels of a molten binder, for example, 8% or more, necessary to prepare the granules and to obtain the desirable release profiles over time. Indeed, the use of wax as a binder is known to impede the release of the active agent and, thus, yield a sustained release product. The use of lower levels of wax is not suggested since the aim of the sustained release product is to impede release.

Described herein are several advantages and unexpected properties of a granule comprising a lower level of wax and a poorly water-soluble active agent. Surprisingly, the lower amount of wax employed herein still provides excellent friability upon compression of the granule to form a pharmaceutical composition. However, unlike compositions in the art, the amount of wax described herein does not substantially alter the immediate release properties of the tablet made from the granules.

An advantage of the present pharmaceutical compositions is that the compressibility of the granules is excellent while retaining an immediate release profile. In other words, the release profile is not appreciably extended or sustained. This is a surprising benefit since the hot melt granules would be expected to have an extended release profile. However, the excellent compressibility of the granules shown herein provides for an ability to prepare tablets containing a poorly water-soluble, i.e., slightly water-soluble or water-insoluble active agent while exhibiting desired friability that also exhibit immediate release of the active agent therein. Such properties were not known to co-exist with slightly water soluble or water insoluble active agents and low levels of wax. Lourdes Ochoa, et al.: "Preparation of sustained release hydrophilic matrices by melt granulation in a high-shear mixer," Journal of Pharmacy and Pharmaceutical Sciences, 8 (2): 132-140, 2005; Yingxu Pend, et al., US2007/0048364; and Mostafa Abarieh, et al., US2010/0120723. In compositions other than the inventive compositions disclosed herein, direct compression can result in unacceptable friability and wet or dry granulation can result in undesirable dissolution properties and bioavailability.

The terms "active agent," "pharmacologically active agent," and "drug" are used interchangeably herein to refer to any chemical compound, which can be an Active Pharmaceutical Ingredient (API), complex or composition that has a beneficial biological effect, preferably a therapeutic effect in the treatment of a disease or abnormal physiological condition. The terms also encompass pharmaceutically acceptable, pharmacologically active derivatives of those active agents specifically mentioned herein, including, but not limited to, salts, esters, amides, prodrugs, active metabolites, isomers, fragments, analogs, and the like. When the terms "active agent," "pharmacologically active agent" and "drug" are used, then, or when a particular active agent is specifically identified, it is to be understood that applicants intend to include the active agent per se as well as pharmaceutically acceptable, pharmacologically active salts, esters, amides, prodrugs, active metabolites, isomers, fragments, analogs, etc.

As used herein, the term "poorly water-soluble," "water insoluble" or "slightly water soluble" and like terms refer to active agents that are sparingly soluble in water. The determination of water solubility is described by the United States Pharmacopeia. As used herein, the term "water insoluble" is used to describe active agents having a solubility in water of about 10,000 parts (parts water per 1 part solute) or <0.1 mg/ml. As used herein, "slightly water soluble" or "poorly water-soluble" are used to describe active agents having a solubility in water of from about 1,000 parts to about 10,000 parts (parts water per 1 part solute) or from about 0.1 mg/mL to about 1 mg/ml.

The term "friability" refers to "tablet friability." A discussion of tablet friability is presented in the US Pharmacopeia. Tablet friability is defined as the percentage value of weight loss due to abrasion. A maximum weight loss of not more than 1% of the weight of the tablets being tested during the friability test is considered generally acceptable. However, a higher friability may be acceptable in certain instances. If a tablet is too friable, it will chip or break during packaging and transport. Conventional rapidly disintegrating tablets are typically formed by compression (e.g., in a tablet press). It is desirable for such tablets to have sufficiently high hardness and sufficiently low friability to provide structural stability for transportation and storage. Low friability (which is measured based on the percent tablet weight loss after a certain number of revolutions in a friabilator) is desirable in that it is generally indicative of high tablet strength. Tablet "hardness" is physical strength measurement of the tablet. The resistance of a tablet to chipping, abrasion, or breakage under conditions of storage, transportation and handling before usage depends on its hardness, or "crushing strength." The tablet "crushing" or "tensile" strength is defined as the force required to break a tablet by compression in the radial direction. It is typically measured using one of the many commonly available tablet hardness testers.

The term "pharmaceutical product" and "dosage form" denote any form of a pharmaceutical composition that contains an effective amount of active agent. When the formulation is a tablet or capsule, the dosage form is usually one such tablet or capsule. The frequency of administration that will provide the most effective results in an efficient manner without overdosing will vary with the characteristics of the particular active agent, including both its pharmacological characteristics and its physical characteristics, such as hydrophobicity.

As used herein, the term "granule" is understood to be a solid constituted by agglomerates of particles or powders of small size, which may have an irregular or spherical shape. Granules can be used as intermediate products in the manufacture of a pharmaceutical form, and they may also be used as an end product. As is known in this field, granules are distinguishable from particles at least by size, morphology or both.

The term "wax" refers to poorly water-soluble or water-insoluble fatty, paraffin-like material. Preferred examples are pharmaceutically acceptable synthetic or natural fatty acids and derivatives thereof. The fatty acid can be in the form of derivatives such as esters like glyceryl monostearate, glyceryl distearate and the like. As used herein, "wax" or "waxy" specifically refers to a component having a melt temperature above room temperature.

As used herein, an "immediate release" refers to a formulation that releases greater than or equal to about 75% of the pharmaceutical agent in less than or equal to about 90 minutes. In embodiments, the release is greater than or equal to release of about 75% of the pharmaceutical agent in less than or equal to about 60 minutes, about 55 minutes, about 50 minutes, about 45 minutes, about 40 minutes, about 35 minutes, about 30 minutes, about 25 minutes, about 20 minutes, about 15 minutes, about 10 minutes or about 5 minutes.

The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period. By "extended period of time" it is meant a continuous period of time of greater than about 90 minutes, preferably, greater than about 4 hours, more preferably, greater than about 8 hours, more preferably greater than about 12 hours, more preferably still, greater than about 16 hours up to more than about 24 hours. The term "delayed release" is used in its conventional sense to refer to a drug formulation in which there is a time delay provided between oral administration of a drug dosage form and the release of the drug therefrom. "Delayed release" may or may not involve gradual release of drug over an extended period of time, and thus may or may not be "sustained release." Preferred "delayed release" formulations are enterically coated compositions. The term "controlled release" refers to a drug-containing formulation or fraction thereof in which release of the drug is not immediate after administration, i.e., with a "controlled release" formulation, administration does not result in immediate release of the drug. However, in an enteric composition, for example, once the enteric coating erodes in the intestines, the release profile may be an immediate release of all of the active agent in the intestines.

In an embodiment, the subject matter disclosed herein is directed to a pharmaceutical composition comprising a granule, wherein the granule comprises a water insoluble active agent or a poorly water-soluble active agent, and a wax material. The pharmaceutical composition exhibits an immediate release profile of the active agent contained therein.

Useful active agents are those that have water solubility of less than 1 mg/ml. Preferably, the active agent(s) has/have water solubility of from about 0.1 mg to about 1 mg/ml. Most preferably, the active agent(s) has/have water solubility of less than 0.1 mg/ml. Preferred active ingredients are selected from the group consisting of disulfiram, felbamate, bicalutamide, raloxifene, fenofibrate, anastrozole, rifaximin and dutasteride. Most preferably, the active agent is disulfiram.

The amount of active agent present in the pharmaceutical composition will depend on the agent. Most useful agents are indicated for certain diseases and conditions and the dose amount of active agent can be readily determined and a pharmaceutical composition comprising the desired amount can be prepared as disclosed herein. Useful values of active agents are from about 1 mg to about 1,500 mg active agent per dosage form of the pharmaceutical composition. Preferred values are from about 200 mg to about 800 mg. In the case of disulfiram, the active agent is preferably present in an amount of from 100 mg to about 1000 mg per dosage form. More preferably, the disulfiram is present in an amount of from about 200 mg to about 800 mg per dosage form. Most preferably, the disulfiram is present in an amount of about 250 mg or about 500 mg and the dosage form is a tablet.

The wax (paraffin) material is a fatty material that has a melting temperature above 20° C. Useful waxes can include carboxylic acids and derivatives thereof, such as $C_{10}$-$C_{20}$ fatty acids. Preferred waxes are selected from the group consisting of is selected from the group consisting of stearic acid, carnauba wax, glyceryl behenate, glyceryl monostearate, glyceryl distearate and gelucire. Useful amounts of wax include an amount of below about 8% (w/w). Preferably, the wax is present in an amount of below about 6% (w/w). Another preferred amount of wax is from about 2% to about 7% (w/w) or from about 2% to about 6% (w/w). Another preferred amount of wax is from about 3% to about 5% (w/w). Another most preferred amount of wax is from about 4% to about 5% (w/w). In embodiments, the wax material may contain more than one wax. Whether the wax material contains one or more different waxes, in preferred embodiments, the wax material comprises stearic acid or derivatives thereof. Preferably, stearic acid is present in amounts not less than 30% of the wax material. More preferably, stearic acid is present in amounts not less than 40% of the wax material. Another useful wax is palmitic acid or derivatives thereof.

The pharmaceutical composition can be in any solid form including capsules, tablets, caplets, rectal or vaginal suppositories, pills, dragees, lozenges, granules, beads, microspheres, pellets and powders, or any combination thereof. Oral administration can be accomplished using other dosage forms including but not limited to capsules, tablets and caplets. Such dosage forms are prepared using conventional methods known to those in the field of pharmaceutical formulation and described in the pertinent texts, e.g., in *Remington: The Science and Practice of Pharmacy* (2000), supra. Oral administration is preferred in the form of a tablet. Preferably, the pharmaceutical composition in the form of a tablet is for immediate release of the active agent contained therein. The tablet also exhibits advantageous properties described herein such as low friability. Lingual and sublingual dosage forms and administration are also contemplated. The sublingual and lingual dosage units are fabricated to disintegrate rapidly. The disintegration time for an exemplary tablet should preferably not be more than about 15 minutes. The time period for complete disintegration of the dosage unit is typically in the range of from about 10 seconds to about 30 minutes, and optimally is less than 5 minutes. The dosage form may be a capsule, in which case the active agent-containing composition may be encapsulated. Suitable capsules may be either hard or soft, and are generally made of gelatin, starch, or a cellulosic material, with gelatin capsules preferred. Two-piece hard gelatin capsules are preferably sealed, such as with gelatin bands or the like. See, for e.g., *Remington: The Science and Practice of Pharmacy* (2000), supra, which describes materials and methods for preparing encapsulated pharmaceuticals. Capsules may, if desired, be coated so as to provide to delay the immediate release of the granules. Dosage forms with delayed release coatings may be manufactured using standard coating procedures and equipment. Such procedures are known to those skilled in the art and described in the pertinent texts (see, for e.g., *Remington: The Science and Practice of Pharmacy* (2000), supra). Generally, after preparation of the capsule, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof. Once the delayed or enteric coating erodes, immediate release of the active can occur.

In an embodiment, the subject matter disclosed herein is directed to a pharmaceutical formulation comprising from about 30% to about 70% (w/w) slightly water soluble and/or water-insoluble active agent; from about 2% to about 8% (w/w) of a wax material; and from about 22% to about 68% pharmaceutically acceptable excipients, such as fillers, disintegrants, lubricants and glidants. The useful and preferred amount of each component is as described elsewhere herein.

In an embodiment, the subject matter disclosed herein is directed to a granule having a water insoluble active agent and an amount of wax material below about 8% (w/w) wherein the granule is compressible to prepare a tablet having acceptable friability and/or hardness properties. The useful and preferred active agents and wax materials and amounts of both are as described elsewhere herein. Preferably, the active agent and wax components of the granule are distributed throughout the granule as opposed to a particle or granule having a wax coating on the surface.

Granules are agglomerates and are therefore generally larger than particles. Measuring the average size of granules refers to an average dimension wherein a certain % of granules are not larger than a target size. Size can be measured by either laser diffraction sizer analysis or mechanical siever such as Ro-Tap. In a preferred embodiment, the final blend granule is of a size that will pass through a #18 mesh screen.

The granules disclosed herein advantageously are capable of being compressed into tablets that exhibit excellent friability while the tablets themselves exhibit an immediate release profile of the active agent. The methods disclosed herein prepare granules that have excellent compressibility, desirable friability and processability, which resolves problematic sticking and baking phenomena during compression. Significantly, heretofore, compressing the active agents disclosed herein into a tablet having acceptable friability would have resulted in a controlled release of the active agent at least because of the excipients required to attain the desired friability. However, when the granules disclosed herein are compressed into a tablet, the tablet exhibits a friability of not more than about 1% and has an immediate release profile for the slightly water soluble or water-insoluble active agent contained therein. Preferably, the tablet exhibits a friability of not more than about 0.2%. Other preferred values for friability are:not more than about 0.9, 0.8, 0.7, 0.6, 0.5, 0.4, 0.3, 0.2 or 0.1% or lower. Most preferably, the tablet exhibits a friability of not more than about 0.1%.

In an embodiment, the subject matter disclosed herein is directed to a tablet comprising compressed granules, wherein the granules comprise from about 2% to below about 8% (w/w) wax material and an active agent having water solubility of less than 1 mg/ml, wherein the tablet has a friability of less than about 1%.

The tablet comprises from about 30% to about 70% (w/w) poorly water-soluble, slightly water-soluble and/or water-insoluble active agent; from about 2% to below about 8% (w/w) of a wax material; and from about 22% to about 68% pharmaceutically acceptable excipients, such as fillers, disintegrants, lubricants and glidants. Preferably, the tablet comprises from about 40% to about 60% (w/w) poorly water-soluble, slightly water-soluble and/or water-insoluble active agent; from about 2% to about 7% (w/w) of a wax material; and from about 33% to about 58% pharmaceutically acceptable excipients, such as fillers, disintegrants, lubricants and glidants, each excipient can be present in any amount such that the total amount of excipients is within the specified range. Most preferably, the tablet comprises from about 45% to about 55% (w/w) poorly water-soluble, slightly water-soluble and/or water-insoluble active agent; from about 2% to about 6% (w/w) of a wax material; and from about 49% to about 53% pharmaceutically acceptable excipients, such as fillers, disintegrants, lubricants and glidants. Preferably, fillers can are present in an amount of from about 40% to about 50% (w/w); disintegrants are present in an amount of from about 4% to about 10% (w/w); lubricants are present in an amount of from about 0.1% to about 1% (w/w) and glidants are present in an amount of from about 0.1% to about 0.5% (w/w). A particularly preferred tablet comprises about 52% disulfiram, 4% wax, such as stearic acid or derivatives thereof, about 36% fillers, such as microcrystalline cellulose and lactose anhydrous; about 6% disintegrant, such as sodium starch glycolate, about 0.5% glidant, such as colloidal silicon dioxide and about 0.25% lubricant such as magnesium stearate.

In another embodiment, the subject matter disclosed herein is directed to a method of preparing a granule comprising an active agent having a water solubility less than about 1 mg/mL, said method comprising, a) contacting a poorly water-soluble, slightly water-soluble or water-insoluble active agent with a liquid wax material, wherein the liquid wax material may contain excipients; b) forming a granulation mix comprising the active agent and the wax material; and c) allowing the mixture to cool to prepare said granules.

In this embodiment, useful temperatures of the liquid wax material prior to contacting it with the active agent are from about 21° C. to about 110° C. Preferably, the temperature of the liquid wax material is from about 40° C. to about 100° C. More preferably, the temperature of the liquid wax material is from about 60° C. to about 95° C. Most preferably, the temperature of the liquid wax material is from about 85° C. to about 95° C.

The contacting of the active agent and the wax material is performed at any temperature that is practical, but is noted that the active agent may be sensitive to excess heat. Preferably, the contacting occurs at a temperature from about 21° C. to about 70° C. More preferably, the contacting occurs at a temperature from about 30° C. to about 60° C. Most preferably, contacting occurs at a temperature from about 35° C. to about 50° C. For example, when the active agent is disulfiram, the contacting can occur at temperatures ranging from about 35° C. to about 50° C., preferably at about 40° C., wherein a granulation mix containing disulfiram is prepared.

Melt agglomeration is a process where granules are bound together to form agglomerates. A molten binder is used to bind the granules into larger agglomerates. Preferably, a high shear mixer is employed. Here, the binder is preferably added as a molten liquid wax, but could be added as a solid that becomes fluid-like as a result of the heat of the process. The method of preparing the granules using a hot melt method is straightforward and efficient.

In this embodiment, since the wax is in a liquid state, the temperature of the liquid is at or above the melting temperature of the wax. The liquid wax is contacted with the active agent to form a granulation mix. The mix can be contained in a granulator as is well-known in the art. A planetary mixer may be used in granulation. Preferably, the granulation mix is prepared in a commercially available granulator. The granulator may be equipped with a heat jacket. Most preferably, the granulator is a hot melt granulator. Preferably, the active agents are granulated with high shear mixer granulation.

Granulation processes provide enlarged granules but can differ in the apparatuses used and the mechanism of the process operation. As used herein, the term "contacting" includes blending, mixing, massing, combining and the like of the ingredients. In high shear granulation (HSG), blending and wet massing is accomplished by high mechanical agitation by an impeller and a chopper. Mixing, densification, and agglomeration of wetted materials are achieved through shearing and compaction forces exerted by the impeller. The primary function of the chopper is to cut lumps into smaller fragments and aid the distribution of the liquid binder. The liquid binder is either poured into the bowl or sprayed onto the powder to achieve a more homogeneous liquid distribution. On the other hand, fluidization is the operation by which fine solids are transformed into a fluid-like state through contact with air. At certain air velocities, the fluid will support the particles, giving them freedom of mobility without entrainment. Such a fluidized bed resembles a vigorously boiling fluid, with solid particles undergoing extremely turbulent motion, which increases with air velocity. Fluidized bed granulation is then a process by which granules are produced in fluidized bed by spraying a binder solution onto a fluidized powder bed to form larger granules. The binder solution can be sprayed from, e.g., a spray gun positioned at any suitable manner (e.g., top or bottom). The spray position and the rate of spray may depend on the nature of the active agent and the binder used, and each is readily determinable by those skilled in the art.

In contrast to a hot melt granulation process, a wet granulation process, preparation comprises the following steps (1) blending the mixture of the active agent and other required pharmaceutically acceptable additives to make a uniform homogenous blend; (2) adding a wetting agent to granulate the uniform blend; (3) drying and sizing the resulting granules to an optimum size suitable for compression; (4) blending the sized granules with the required pharmaceutically acceptable additives/lubricants; and finally (5) compressing the blended granules into tablets. Dry granulation refers to the granulation of a formulation without the use of heat and solvent. Dry granulation technology generally includes slugging or roll compaction. Slugging consists of dry-blending a formulation and compressing the formulation into a large tablet or slugs on a compressing machine. The resulting tablets or slugs are milled to yield the granules. Roller compaction is similar to slugging, but in roller compaction, a roller compactor is used instead of the tableting machines. See, e.g., Handbook of Pharmaceutical Granulation Technology, D. M. Parikh, eds., Marcel-Dekker, Inc. pages 102-103 (1997). Dry granulation technique is useful in certain instances, e.g., when the active agent is sensitive to heat or solvent.

After forming the granulation mix, it is allowed to cool either by simply exposing the mix to a lower temperature, such as, for example, room temperature. Cooling of the granulation mix may be carried out using a fluidized bed drier or tray drier. The cooling of the mix results in the formation of granules. As discussed herein, the granules can be made into agglomerates.

After granulation, optionally, the granulated formulation can be milled. Milling can be performed using any suitable commercially available apparatus (e.g., Fitzmill equipped with a #1 screen). The mesh size for the screen can be selected depending on the size of the granules desired.

After granulation and milling, if performed, the granules can be blended with other ingredients to prepare a final blend. For example, to prepare tablets, certain excipients are added to the granules to further facilitate forming the tablet. However, if the granules themselves are not sufficiently compressible, the amount or nature of the excipients needed to be added for compressibility will adversely impact the properties of the final pharmaceutical formulation. An advantage of the presently disclosed granules is that they are readily compressible and therefore preparing the final blend is straightforward. The final blend will have a tap density of from about 0.1 to about 1.5 g/cc, preferably from about 0.3 to about 1.2 g/cc and most preferably from about 0.55 to about 0.95 g/cc. The result is a compressible, immediate release granule containing a slightly water soluble or water-insoluble active agent.

The tablet may contain other conventional ingredients, including other pharmaceutically acceptable excipients, such as fillers, which include water-soluble compressible carbohydrates such as dextrose, sucrose, mannitol, sorbitol, maltitol, xylitol, lactose, lactose anhydrous (DT) and mixtures thereof; other conventional dry binders like polyvinyl pyrrolidone and the like; sweeteners such as aspartame, acesulfame potassium, sucralose, and saccharin; and lubricants. The mixture may also incorporate pharmaceutically acceptable adjuvants, including, for example, preservatives, flavors, antioxidants, surfactants, and coloring agents.

The tablet may contain diluents that possess no therapeutic value, but add physical characteristics to a pharmaceutical composition. Diluents can include microcrystalline cellulose, powdered cellulose, lactose, starch, mannitol, dextrose, sucrose and dibasic calcium phosphate. Preferred diluents are microcrystalline cellulose, powdered cellulose, and lactose.

Other optional ingredients in the composition include but are not limited to pharmaceutically acceptable excipients such as cellulose polymers or carbohydrates, lubricants, compacting agents and glidants, such as colloidal silicon dioxide (Cab-O—Sil®, M5P). Useful lubricants include talc, calcium stearate, magnesium stearate, sodium stearyl fumarate, stearic acid, magnesium stearate, solid polyethylene glycols and cocoa butter.

Any known disintegrants such as crospovidone, carboxymethylcellulose, sodium starch glycolate, croscarmellose sodium, N.F. (a cross linked sodium carboxymethyl cellulose material), or mixtures thereof may be used as well.

One more binders, fillers or extenders such as starches, lactose or other sugars, polyvinylpyrrolidone, sodium citrate, dicalcium phosphate and other alkaline inorganic salts, carboxylmethylcellulose and other cellulose polymers, alginates, gelatins, microcrystalline cellulose, sorbitol, sodium chloride, chitosan, hydrogenated vegetable oil, kaolin, glycerol palmitostearate, magnesium carbonate, and calcium carbonate may also be employed.

When preparing the formulation as described above in the form of a tablet, the granules are compressed into a tablet form. The tablet shaping can be done by any suitable means, with or without compressive force. For example, compression of the formulation after the granulation step can be accomplished using any tablet press, provided that the tablet composition is adequately lubricated with a lubricant such as magnesium stearate.

The granules described herein are advantageously compressible, whereas direct compression consists of compressing tablets directly from powdered material without modifying the physical nature of the material itself. The compression force can be selected based on the type/model of press, what physical properties are desired for the tablets product (e.g., desired hardness, friability, etc.), the desired tablet appearance and size, and the like. The size of the tablet can be any desirable size corresponding to an appropriately sized molds, dies and punches.

Tablet hardness constitutes another important pharmacotechnical property during tablet manufacture. Tablet hardness is associated with several tablet properties, including density and porosity. Hardness generally increases with normal storage of tablets, and depends on the shape, chemical properties, binding agent, as well as pressure applied during compression. If a tablet is too hard, then it may not disintegrate in the required period of time to meet the dissolution specifications. In contrast, if a tablet is too soft, then it may not be able to withstand the handling during subsequent processing, such as coating or packaging. Preferably, the tablet is also relatively hard after tableting. Hardness is a term used in the art to describe the diametral breaking strength as measured by conventional pharmaceutical hardness testing equipment, such as a Schleuniger Hardness Tester. In order to compare values across different size tablets, the breaking strength is normalized for the area of the break. This normalized value, expressed in $kp/cm^2$, is sometimes referred in the art as tablet tensile strength. See, Leiberman et al., Pharmaceutical Dosage Forms—Tablets, Volume 2, 2nd ed., Marcel Dekker Inc., 1990, pp. 213-217, 327-329.

Typically, the compression force applied is such that the compressed tablets have a hardness of at least about 2 kp and a maximum hardness of about 20 kp. Preferably, the maximum hardness is 18.0 kp. These tablets generally provide sufficient hardness and strength to be packaged, shipped or handled by the user. If desired, a higher compression force can be applied to the tablet to increase the tablet hardness.

However, the compression force is preferably selected so that the tablet is not overcompressed where weak points in the internal structure within the tablet result in increased or undesirable tablet friability. Preferably, the compression force applied is such that the compressed tablet has a hardness of less than about 14 kp. In certain embodiments, it may be preferred to compress a tablet to a hardness of between about 5 kp to about 11 kp, optionally between about 7 kp to about 9 kp, or about 8 kp.

The compression step can be carried out using a rotary type tablet press. The rotary type tableting machine has a rotary board with multiple through-holes, or dies, for forming tablets. The formulation is inserted into the die and is subsequently press-molded. The diameter and shape of the tablet depends on the molds, dies and punches selected for the shaping or compression of the granulation composition. Tablets can be discoid, oval, oblong, round, cylindrical, triangular, and the like. The tablets may be scored to facilitate breaking. The top or lower surface can be embossed or debossed with a symbol or letters.

Parameters of tablets such as hardness, friability, and thickness, can be measured to ensure the results meet the prerequisites of established acceptance criteria.

The dosage form of the invention is preferably stable in the sense that it does not significantly change after manufacture with respect to physical and chemical properties e.g. mechanical robustness and organoleptic properties in order to ensure a sufficient shelf life of the final product.

In an embodiment, the subject matter disclosed herein is directed to a method of treating a subject comprising administering an inventive pharmaceutical formulation as disclosed herein to the subject. The preferred slightly water soluble or water-insoluble active agents used in the pharmaceutical compositions, granules and methods disclosed herein are known for treating certain diseases and/or medical conditions, e.g., disulfiram is indicated for chronic alcoholism, felbamate is indicated for epilepsy and psychiatric conditions, bicalutamide is indicated for prostate cancer, raloxifene is indicated for osteoporosis, fenofibrate is indicated for hypercholesterolemia and hypertriglyceridemia, anastrozole is indicated for early-stage, receptor-positive breast cancer, rifaximine is an antibiotic and dutasteride is indicated for benign prostatic hyperplasia. Thus, the effective amount and dosage of such active agents required to be administered for effective treatment are known in the art or can be readily determined by those of skill in this field. Where active agents do not have a known dosage for certain diseases, the effective amount of active agent and the amount of a particular dosage form required to be administered for effective treatment can be readily determined by those of skill in this field. By an "effective" amount or a "therapeutically effective amount" of an active agent is meant a nontoxic but sufficient amount of the agent to provide the desired effect. Of course, the amount of active agent administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art coupled with the general and specific examples disclosed herein.

The term "subject" refers to a mammal, which means humans as well as all other warm-blooded mammalian animals. As used herein, the term "mammal" includes a "patient." As used herein "a mammal in need thereof" may be a subject whom could have been but is not required to have been diagnosed as suffering from the condition intended to be treated.

The term "treating" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual by inhibiting or causing regression of a disorder or disease. As used herein the terms "treating" includes "ameliorating," which refers to all processes wherein there may be a slowing, interrupting, arresting, or stopping of the progression of the condition or symptoms and does not necessarily indicate a total elimination of the underlying condition.

The present subject matter is further described herein by the following non-limiting examples which further illustrate the invention, and are not intended, nor should they be interpreted to, limit the scope of the invention.

EXAMPLES

1. Tablet Formulations Prepared by Hot Melt Granulation

Example 1

Stearic acid (150.0 g, including 50% overage) was molten at a temperature around 85° C. (heated at about 85° C. to 95° C.) and then 100.0 g of the molten liquid was added to the granulation ingredients (disulfiram 1000.0 g) in the bowl of a granulator under mixing. Mixing was continued until an acceptable granulation was obtained. The hot melt granulation was cooled in a tray until desired product temperature (NMT 35° C.) was achieved, and then the cooled granulation was passed through a Fitzmill to attain proper size distribution. Part of the granules (440.0 g) were blended with the extragranularly added ingredients (Lactose Monohydrate, 136.0 g; microcrystalline cellulose, 136.0 g; sodium starch glyoclate, 42.3 g; Magnesium stearate, 1.9 g and colloidal silicon dioxide, 3.8 g) and the blend was compressed into tablets.

Example 2 and Example 3 were manufactured using the process similar to the one in Example 1, except that the process followed in Example 3 used a fluid bed to cool the hot melt granulation.

TABLE 1

Examples of Disulfiram Tablet Formulations made by Hot Melt Granulation Process

| | % w/w | | |
|---|---|---|---|
| Ingredients | Example 1 | Example 2 | Example 3 |
| Molten Liquid Ingredients: | | | |
| Stearic Acid | 5.3 | 5.3 | 4.2 |
| Granulation Ingredients: | | | |
| Disulfiram | 52.6 | 52.6 | 52.6 |
| Lactose Anhydrous | — | 7.9 | 8.4 |
| Microcrystalline Cellulose | — | 7.9 | 8.4 |
| Extragranularly Added Ingredients | | | |
| Lactose Anhydrous | 17.9 | 10.0 | 10.0 |
| Microcrystalline Cellulose | 17.9 | 10.0 | 10.0 |

TABLE 1-continued

Examples of Disulfiram Tablet Formulations made by
Hot Melt Granulation Process

| Ingredients | % w/w | | |
|---|---|---|---|
| | Example 1 | Example 2 | Example 3 |
| Sodium Starch Glycolate | 5.6 | 5.6 | 5.6 |
| Magnesium Stearate | 0.25 | 0.25 | 0.25 |
| Colloidal Silicon Dioxide | 0.5 | 0.5 | 0.5 |
| Total | 100 | 100 | 100 |

2. Comparison of Hot Melt Granulation and Direct Compression Processes

Example 3 above was compared to a direct compression tablet, Example 4.

Example 4(Comparative Example)

Magnesium stearate, 2.4 g and the colloidal silicon dioxide, 4.0 g were added to a V-blender, blended for 3 min to produce a Part I lubricant pre-blend, which was discharged and passed through a #18 screen. Additional ingredients 175.0 g microcrystalline cellulose, 52.9 g sodium starch glycolate, 45.0 g stearic acid, 500.0 g disulfiram and 170.0 g lactose anhydrous were individually passed through a #18 mesh. The screened microcrystalline cellulose, screened sodium starch glycolate, screened stearic acid, screened disulfiram and screened lactose anhydrous, were added into the same V-blender and blended for ten (10) minutes to produce the blend. The blend was discharged and passed through a Fitzmill to de-lump and improve the mixing efficiency. Approximately half of the milled blend, the screened lubricant pre-blend, and the remaining milled blend was added to the same V-blender above and blended for fifteen (15) minutes to produce the final blend. The final blend was then compressed into tablets.

TABLE 2

Examples of Disulfiram Tablet Formulations made by
Direct Compression compared to Tablets made by
Hot Melt Granulation

| | w/w % | |
|---|---|---|
| Formulation | Example 3 Hot Melt Granulation | Example 4 Direct Compression |
| Part I | | |
| Stearic Acid | 4.21 | 4.74 |
| Disulfiram | 52.63 | 52.63 |
| Microcrystalline Cellulose | 8.42 | — |
| Lactose Anhydrous | 8.42 | — |
| Part II | | |
| Microcrystalline Cellulose | 10.0 | 18.42 |
| Lactose Anhydrous | 10.0 | 17.89 |
| Sodium Starch Glycolate | 5.57 | 5.57 |
| Colloidal Silicon Dioxide | 0.50 | 0.50 |
| Magnesium Stearate | 0.25 | 0.25 |
| Total | 100.0 | 100.0 |
| Performance | | |
| Maximum Hardness (kp): | 18.0 | 16.8 |
| Friability (%) (14 kp tablets) | 0.1 | 0.2 |
| Observations on Processability: | acceptable | sticking on punches and tablet press |

3. Wet Granulation Formulation

Example 5(Comparative Example)

Part I povidone was dissolved into Part I purified water in an appropriate container to produce the Part I granulation solution. Part II disulfiram, Part II microcrystalline cellulose, Part II pregelatinized starch, Part II croscarmellose sodium and Part II sodium starch glycolate was loaded into a fluid bed. The dry mixture was granulated in the fluid bed by top spray using the Part I granulation solution. The part I and part II material was divided into multiple repeated sub-parts for granulation based on the fluid bed capacity. The dried granulation was then passed through a Fitzmill for proper size distribution. Part III colloidal silicon dioxide and Part III magnesium stearate were added into a V-blender, blended for 3 minutes and discharged. The blend was passed through an 18-mesh screen to produce the lubricant pre-blend. The milled granules were added along with the rest of the Part III ingredients, microcrystalline cellulose, sodium starch glycolate and croscarmellose sodium, into the same V-blender and mixed for 10 minutes. The lubricant pre-blend was added and mixing continued for 5 minutes to produce the final blend. The final blend was then compressed into tablets.

TABLE 3

Example of Disulfiram Tablet Formulations made by
Wet Granulation Process

| Ingredients | % w/w Example 5 Wet Granulation |
|---|---|
| Part I (Granulating Solution) | |
| Povidone | 2.11 |
| Purified Water, USP | — |
| Part II | |
| Disulfiram | 52.63 |
| Microcrystalline Cellulose | 12.63 |
| Pregelatinized Starch | 8.42 |
| Croscarmellose Sodium | 3.58 |
| Sodium Starch Glycolate | 3.58 |
| Part III | |
| Microcrystalline Cellulose | 8.84 |
| Sodium Starch Glycolate | 3.58 |
| Croscarmellose Sodium | 3.58 |
| Magnesium Stearate | 0.63 |
| Colloidal Silicon Dioxide | 0.42 |
| Core Tablet Weight | 100.0 |

4. Bioavailability of Wet Granulation Formulation and Hot Melt Formulation

The hot melt granulation formulation (Example 3) exhibited bioequivalence while the wet granulation formulation (Example 5) showed about 10% (barely significant) faster drug release in all media.

TABLE 4

Bioavailability of Disulfiram Tablets, 500 mg, as Compared to Antabuse® (Test/Reference Ratio), under Fasting Conditions

| Wet Granulation Formulation vs Antabuse® | | |
|---|---|---|
| Antabuse® 500 mg Vs. | Cpeak, Mean (90% C.I.) | AUCL, Mean (90% C.I.) |
| Example 5 (wet granulation) | 134 (119-151) | 131 (121-141) |
| Hot Melt Formulation vs Antabuse® | | |
| Antabuse® 500 mg Vs. | Cpeak, Mean | AUCL, Mean |
| Example 3 (hot melt granulation) | 101 (93-108) | 101 (95-108) |

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

That which is claimed:

1. An immediate release pharmaceutical composition consisting of granules and extragranular excipients, wherein
   the granules consist of disulfiram, a wax material, microcrystalline cellulose, and lactose;
   the wax material is present in an amount of about 2% (w/w) to about 7% (w/w) of the granules; and
   the disulfiram and the wax material are distributed throughout the granules.

2. The composition of claim 1, wherein said wax is present in an amount from about 3% to about 5% (w/w) of said granule.

3. The composition of claim 1, wherein said wax is selected from the group consisting of stearic acid, palmitic acid, carnauba wax, glyceryl behenate, glyceryl monostearate, glyceryl distearate, and gelucire, and combinations thereof.

4. The composition of claim 1, wherein said wax material comprises at least about 40% w/w stearic acid.

5. The composition of claim 1, wherein said composition is a tablet.

6. The composition of claim 1, wherein said wax material is stearic acid.

7. The composition of claim 1, wherein the extragranular excipients consist of microcrystalline cellulose, lactose, sodium starch glycolate, colloidal silicon dioxide, and magnesium stearate.

* * * * *